(12) United States Patent
Hölderich et al.

(10) Patent No.: US 6,482,945 B2
(45) Date of Patent: Nov. 19, 2002

(54) PROCESS FOR PRODUCING EPSILON-CAPROLACTAM AND APPARATUS FOR THE PROCESS

(75) Inventors: Wolfgang F. Hölderich, Frankenthal; Gerd Dahlhoff, Bergheim; Andre Sbresny, Aachen, all of (DE); Hiroshi Ichihashi, Otsu (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/964,424

(22) Filed: Sep. 28, 2001

(65) Prior Publication Data

US 2002/0040137 A1 Apr. 4, 2002

(30) Foreign Application Priority Data

Sep. 29, 2000 (JP) .................................... 2000-300264

(51) Int. Cl.$^7$ ............................................ C07D 201/04
(52) U.S. Cl. ...................................................... 540/536
(58) Field of Search ........................................ 540/536

(56) References Cited

U.S. PATENT DOCUMENTS 4,137,263 A   1/1979   Immel et al. ............ 260/566 A
4,268,440 A   5/1981   Werther et al. ......... 260/239.3 A
6,265,574 B1 * 7/2001  Kitamura et al. ............. 540/536

FOREIGN PATENT DOCUMENTS

| EP | 017 945 A1 | 10/1980 |
| EP | 1 028 108 A1 | 8/2000 |
| GB | 999851 | 7/1965 |
| GB | 1368460 | 9/1974 |
| JP | 47041909 | 2/1970 |

* cited by examiner

*Primary Examiner*—Bruck Kifle
(74) *Attorney, Agent, or Firm*—Birch, Stewart, Kolasch & Birch, LLP (57) ABSTRACT

A process is provided for producing ε-caprolactam from cyclohexanone oxime. The process comprises a evaporation step of a mixture of cyclohexanone oxime and a solvent by introducing the mixture into a fluidized bed in which inert particles is fluidized by an inert gas, the particles having heat enough to evaporate the mixture; and a rearrangement step of cyclohexanone oxime in the evaporated mixture into ε-caprolactam by a gas phase Beckmann rearrangement reaction using a solid catalyst, excluding a catalyst consisting of a boric acid or a boron oxide.

7 Claims, 9 Drawing Sheets

PROCESS FOR PRODUCING EPSILON-CAPROLACTAM AND APPARATUS FOR THE PROCESS

FIELD OF THE INVENTION

The present invention relates to a process for producing ε-caprolactam from cyclohexanone oxime and an apparatus for the process.

BACKGROUND OF THE INVENTION

ε-caprolactam may be used as a monomer for producing Nylon-6, that is a raw material for producing fibers, engineering plastics and the like. ε-caprolactam may be produced by a process in which cyclohexanone oxime is evaporated and is then rearranged into ε-caprolactam in a gas phase Beckmann rearrangement reaction. Heretofore, however, the process has problems such that ε-caprolactam is produced with a relatively high content of by-products such as cyanopentenes, octahydrophenazine and caprenolactam.

For example, United Kingdom (GB) Patent No. 999,851 discloses a process in which cyclohexanone oxime is evaporated in a fluidized bed of an acidic catalyst and is then rearranged into ε-caprolactam using an acidic catalyst. In this process, however, a part of cyclohexanone oxime is decomposed to be cracking products, which results in lowering the purity of the resulting ε-caprolactam. The GB Patent also discloses a process comprising two steps of evaporating cyclohexanone oxime in a falling film evaporator and rearranging the evaporated cyclohexanone oxime in a reactor. This process, however, is insufficient in suppressing the generation of the cracking products.

On the other hand, German Patent 2,641,414 (corresponding to U.S. Pat. No. 4,137,263) discloses an improved method for evaporating cyclohexanone oxime in a falling film evaporator. This process, however, is also insufficient in suppressing the generation of the cracking products since a large amount of cyclohexanone oxime is circulated in the evaporator at high temperature. Also, it is difficult to control evaporation conditions in the evaporator in an industrial scale.

SUMMARY OF THE INVENTION

One objective of the present invention is to provide a process for producing ε-caprolactam with sufficiently reducing the generation of by-products. The present inventors have found that this object and other objects are achieved by a process comprising the steps of evaporating a mixture of cyclohexanone oxime and a solvent in a fluidized bed and rearranging the cyclohexanone oxime into ε-caprolactam, and have accomplished the present invention.

The present invention provides a process for producing ε-caprolactam comprising the steps of evaporating a mixture of cyclohexanone oxime and a solvent by introducing the mixture into a fluidized bed in which inert particles are fluidized by an inert gas, the particles having heat enough to evaporate the mixture; and rearranging cyclohexanone oxime in the evaporated mixture into ε-caprolactam by a gas phase Beckmann rearrangement reaction using a solid catalyst, excluding a catalyst consisting of a boric acid or a boron oxide.

The present invention also provides an evaporator, comprising an evaporation column in which inert particles are fluidized; a pipe for introducing a mixture of cyclohexanone oxime and a solvent into the column; and a heat source for providing the inert particles with heat enough to evaporate the mixture, the heat source being installed at the inside and/or outside of the column.

The present invention further provides an apparatus, comprising an evaporation zone (or evaporator) in which a mixture of cyclohexanone oxime and a solvent is evaporated in a bed of inert particles which are fluidized by an inert gas, the particles having heat enough to evaporate the mixture; and a reaction zone (or reactor) in which cyclohexanone oxime in the evaporated mixture is rearranged into ε-caprolactam by a gas phase Beckmann rearrangement reaction using a solid catalyst, excluding a catalyst consisting of a boric acid or a boron oxide.

DETAILED DESCRIPTION OF THE INVENTION

In the present invention, a mixture of cyclohexanone oxime and a solvent is introduced into a fluidized bed of inert particles. The inert particles, which have heat enough to evaporate the mixture, are fluidized by an inert gas.

The inert particles and the inert gas are both substantially inert to the cyclohexanone oxime and the solvent, and are substantially inactive in gas phase Beckmann rearrangement reaction of cyclohexanone oxime. Examples of the inert gas include nitrogen, argon, methanol and ethanol. Among them, nitrogen and methanol are preferred. Examples of the inert particles include glass particles, silica particles, silicon carbide particles and alumina particles. It is preferred that the specific surface area of the inert particles is small so that the inert particles absorb cyclohexanone oxime as little as possible. Specifically, the specific surface area of the inert particles is preferably about 1 $m^2/g$ or less. The particle diameter and the density of the inert particles are important in easy fluidization of the particles. The particle diameter of the inert particles is preferably in the range of from about 0.02 mm to about 1 mm. The density (i.e., bulk density, which is the weight of particles packed in a 100-ml container) of the inert particles is preferably in the range of from about 0.8 g/ml to about 3 g/ml.

In accordance with the present invention, cyclohexanone oxime evaporates in the mixture containing a solvent, thereby the boiling point of cyclohexanone oxime decreases. Cyclohexanone oxime in the mixture evaporates at a temperature lower than the boiling point of cyclohexanone oxime with no solvent, which results in suppressing the generation of side products (which is due to the adverse reactions in evaporation).

The solvent to be mixed with cyclohexanone oxime in the present invention is a solvent which is able to dissolve cyclohexanone oxime. Examples of the solvent include lower saturated alcohols having 1 to 6 carbon atoms such as methanol, ethanol, propanol and tertiary butanol; aromatic hydrocarbons such as benzene and toluene; acenonitrile; and the like. Among them, methanol and ethanol are preferred. The mixing ratio of cyclohexanone oxime to the solvent (cyclohexanone oxime:solvent) is preferably in the range of from 1:0.5 to 1:10, by weight.

In the present invention, the inert particles may receive heat from a heat source in an amount sufficient to evaporate the mixture and may circulate in a fluidized bed thereof. Once the mixture of cyclohexanone oxime and the solvent is introduced into the fluidized bed, the mixture comes in contact with the surface of the inert particles and rapidly evaporates, which also results in suppressing the generation of side products in evaporation.

The inert particles may be continuously replaced where the mixture is introduced into the fluidized bed of the particles and be continuously re-heated by the heat source. The fluidized bed is preferably in a bubbling state or in a slugging state which generates a vigorous flow of the particles therein, so that the particles are smoothly replaced and re-heated. From the industrial point of view, it is preferred that the fluidized bed is in a bubbling state.

In the evaporation of cyclohexanone oxime, carbonaceous materials (tar-like components) may be generated on the inert particles. The carbonaceous materials may cause the problems such that the carbonaceous materials facilitate the decomposition of cyclohexanone oxime in the mixture and that the carbonaceous materials also evaporate and are mixed with the vapor of cyclohexanone oxime. In the present invention, the inert particles having the carbonaceous material thereon may be regenerated by being treated with an inert gas and/or oxygen-containing gas such as air at a temperature of from about 300° C. to about 600° C. In such a treatment, the carbonaceous material may be removed from the inert particles to regenerate the inert particles. The regeneration step may be carried out after the evaporation step is stopped, or while the evaporation step is simultaneously continued by circulating the inert particles continuously or intermittently between the evaporation step and regeneration step. The latter manner is preferred because of high productivity.

For example, the evaporation step and the regeneration step can be conducted while the inert particles are circulated between an evaporation column and a regeneration column which can prepare a fluidized bed of the particles therein. During the circulation, the inert particles may be regenerated in the regeneration column, while being fluidized by air or the like. Instead of the regeneration column which can prepare the fluidized bed of the particles therein, a kiln (such as a rotary kiln) may be used.

In the present invention, the evaporated mixture of cyclohexanone oxime is subjected to gas phase Beckmann rearrangement reaction in the presence of a solid catalyst, excluding a catalyst consisting of a boric acid or a boron oxide.

The solid catalyst to be used in the present invention may be a crystalline zeolite catalyst such as a crystalline aluminosilicate and crystalline metallosilicate. The crystalline metallosilicate may have a Si/M atomic ratio of about 5 or more, and preferably have a Si/M atomic ratio of about 50 or more, wherein M represents at least one element selected from the group consisting of B, Al, Ga, Fe, Ti and Zr. The Si/M atomic ratio can be measured by atomic absorption analysis, fluorescent X-ray analysis or the like.

Preferable Examples of the crystalline zeolite include a so-called "high-silica" zeolite in which the main element of the zeolite skeleton is substantially silicon; a MFI zeolite containing boron as a main element; and the like.

The solid catalyst to be used in the present invention may have a particle diameter of from about 0.02 mm to about 1 mm, and preferably have a particle diameter of from about 0.02 mm to about 0.5 mm.

In the present invention, Beckmann rearrangement reaction of cyclohexanone oxime may be conducted at a temperature of from about 250° C. to about 500° C., and preferably at a temperature of from about 300° C. to about 400° C. Although not outside the scope of the present invention, when the temperature is lower than about 250° C., the reaction rate may be insufficient and the selectivity to ε-caprolactam tends to decrease. Also again while not outside the scope of the present invention, when the temperature exceeds about 500° C., the thermal decomposition of cyclohexanone oxime tends to increase and the selectivity to ε-caprolactam tends to decrease. The reaction pressure may be any suitable pressure, and is preferably from atmospheric pressure to reduced pressure. The reaction pressure is preferably in the range of from about 5 kPa to about 0.2 MPa, and more preferably in the range of from about 5 kPa to 0.1 MPa.

The space velocity (WHSV) of the raw material, i.e., cyclohexanone oxime, in the reaction may be in the range of from about 0.1 $h^{-1}$ to about 20 $h^{-1}$ in terms of WHSV (which means that the supplying speed of cyclohexanone oxime may be about 0.1 g/hr to about 20 g/hr per 1 g of the catalyst), and is preferably in the range of from about 0.2 $h^{-1}$ to about 10 $h^{-1}$.

In the present invention, cyclohexanone oxime is rearranged with being diluted with the solvent such as a lower alcohol, which results in improvement in the selectivity to ε-caprolactam and in the life of the solid catalyst.

An apparatus utilized for the process of the present invention may comprise a zone (or evaporator) for evaporating the mixture of the cyclohexanone oxime and a zone (or reactor) for rearranging cyclohexanone oxime in the evaporated mixture into ε-caprolactam. The evaporated cyclohexanone oxime, the evaporate solvent and the inert gas are introduced from the evaporated zone (or evaporator) into the reaction zone (or reactor), to conduct gas phase Beckmann rearrangement reaction of cyclohexanone oxime for producing ε-caprolactam.

In the evaporation zone (or evaporator) of the apparatus, a fluidized bed comprising inert particles is prepared with the inert gas. The mixture of cyclohexanone oxime is introduced thereto and evaporated therein. In the reaction zone (or reactor) of the apparatus, particles of the solid catalyst may be packed therein to prepare a fixed bed thereof, or may be fluidized by the mixture of cyclohexanone oxime and the inert gas to prepare a fluidized bed.

The apparatus may be a single column which comprises two zones, i.e., one zone for evaporating the mixture of the cyclohexanone oxime, which may be in a lower part of the column, and the other zone for rearranging cyclohexanone oxime in the evaporated mixture into ε-caprolactam, which may be in an upper part of the column.

When the apparatus is a single column, the evaporation zone and the reaction zone may be separated from each other, each of which is in the lower part and in the upper part of the single column, respectively. Alternatively, a portion of the evaporation zone and a portion of the reaction zone may be overlapped with each other in each layer form. Such partially overlapped layers may be prepared by difference in bulk density or in particle diameter between the inert particles and catalyst particles. That is, when the bulk density and/or particle diameter of the inert particles is larger than the bulk density and/or particle diameter of the catalyst particles, the inert particles having a larger bulk density and/or a larger particle diameter underlies the catalyst particles, to prepare the partially overlapped layers in which the inert particles and the catalyst particles are separated into a lower layer and an upper layer, respectively, while being partially overlapped.

Another apparatus which is utilized for the process of the present invention may comprise an evaporator, a reactor and a pipe connecting the evaporator with the reactor. In the evaporator, the inert particles are fluidized by the inert gas to prepare the fluidized bed thereof. The mixture of cyclohexanone oxime and the solvent is introduced into the evaporator and is evaporated therein. The evaporator may comprise an evaporation column, an introducing pipe and a heat source. In the evaporation column, the fluidized bed of the inert particles may be prepared as described above. The introducing pipe may be inserted into the evaporation column so that the mixture of cyclohexanone oxime and the solvent is injected into the fluidized bed in the column. It is preferred that the introducing pipe is inserted into the evaporation column downward or upward, so as to vertically inject the mixture and so as not to block the flow of the inert particles in the fluidized bed. The heat source may be installed outside and/or inside of the evaporation column so as to supply, to the inert particles, heat energy enough to evaporate the mixture which is injected to the column.

The evaporated mixture of cyclohexanone oxime and the solvent can be sent through the pipe into the reactor, in which the fluidized bed of catalyst particles may be prepared and a gas phase Beckmann rearrangement reaction of cyclohexanone oxime may be carried out to produce ε-caprolactam.

For reference, the present invention is described using FIGS. 1–4, which should not be construed as a limitation upon the scope of the present invention.

Figure 1:
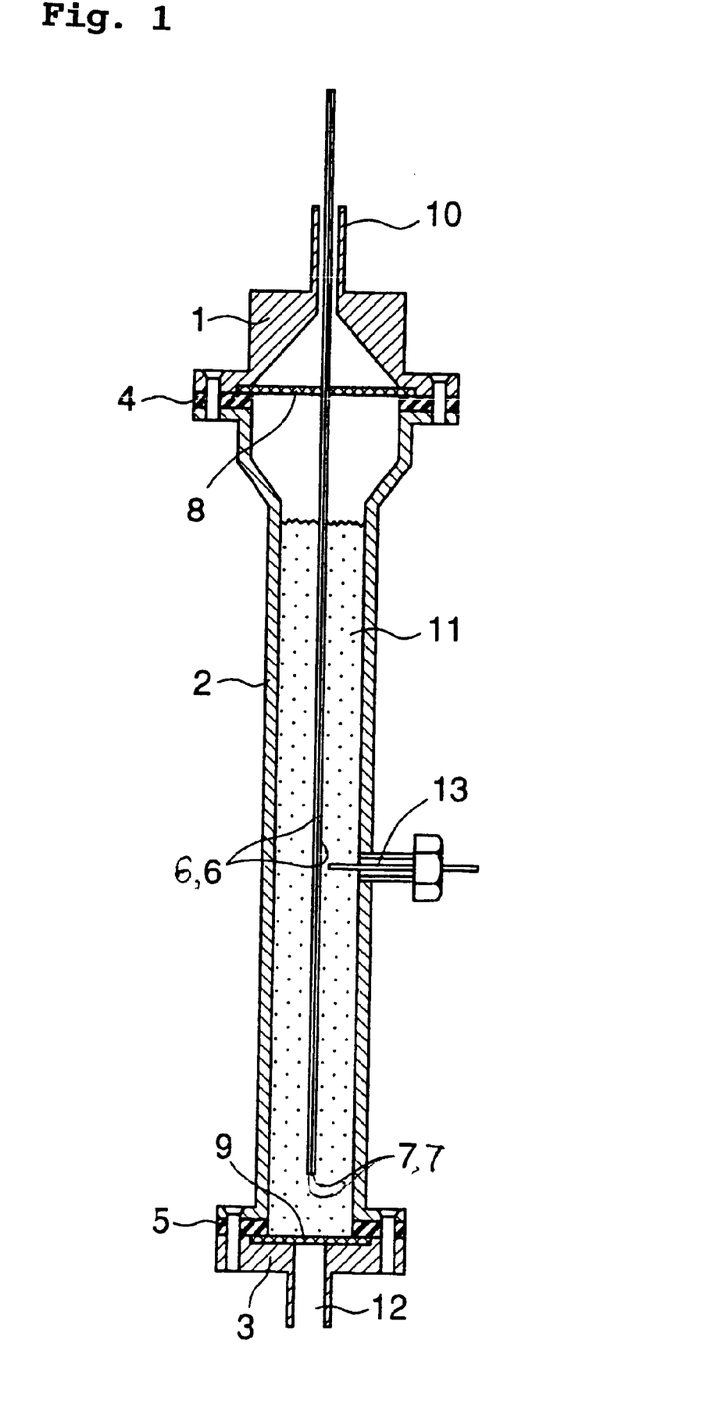
FIG. 1 is a sectional view of an evaporation column which may be utilized in the present invention.

FIG. 1 illustrates a sectional view of one example of an evaporation column, which can be utilized for an evaporator in the present invention.

The evaporation column may be utilized in a mini-plant. The evaporation column comprises components 1, 2 and 3, which are integrally connected with one another by fastening their flanges with a screw or bolt, through sealing materials 4 and 5. Examples of the sealing materials 4 and 5 include tetrafluoroethylene resin and the like.

Component 2 may be made of a steel pipe. The diameter of one end (i.e., an upper end in FIG. 1.) of component 2, facing component 1, is widened. Components 8,9 (such as meshes and gas-permeabile plates) are placed at both ends of component 2, to prevent the inert particles from escaping from the column.

Component 1 has a concave surface which is formed like an inside of a conical surface (see, FIG. 1). The surface can reduce the inside surface area of the outlet of the column and prevent the evaporated mixture from condensing when the mixture is discharged. It is preferred that component 1 has a large heat capacity and is heated from outside, which also prevents the evaporated mixture from condensing.

Component 3, that is the lowermost part of the column, is a gas disperser for introducing the inert gas to component 2. From gas introducing pipe 12 in component 3, an inert gas introduced into the column. By the inert gas, fluidized bed 11 of the inert particles (such as glass particles) is prepared in component 2. The introducing rate of the inert gas is important in a uniform flow of fluidized bed 11 of the inert particles.

Fluidized bed 11 of the inert particles is preferably in a slugging state or a bubbling state. The flat surface of component 9 facilitates to generate a slugging state or a bubbling state of fluidized bed 11, thereby the inert particles may float and be mixed sufficiently with one another in component 2.

Two narrow introducing pipes (such as capillaries) 6, 6 are inserted from injection port 10 at an upper part of the column. The mixture of cyclohexanone oxime and a solvent, each of which is usually in a liquid state, is injected or sprayed into the column as fine droplets thereof into component 2 through introducing pipes 6, 6 using a pump or the like. The mixture is preheated with heat of fluidized bed 11 while the mixture is transferred to injecting ports 7, 7 of introducing pipes 6, 6. At injecting ports 7, 7, the preheated mixture of cyclohexanone oxime is injected into component 2, and evaporates rapidly once the mixture comes in touch with the heated inert particles therein.

The preheating temperature of the mixture in introducing pipes 6, 6 is preferably controlled to be slightly lower than the boiling point of cyclohexanone oxime by adjusting the length of introducing pipes 6, 6. When the preheating temperature is higher than the boiling point of the cyclohexanone oxime in the mixture, the cyclohexanone oxime tends to vaporize in introducing pipes 6, 6, which may result in lowering the performance of the column, i.e., the evaporator shown in FIG. 1.

Through introducing pipes 6, 6, the mixture of cyclohexanone oxime is injected directly into fluidized bed 11. Due to such a direct injection, the mixture rapidly evaporates when it comes contact with the surface of the heated inert particles in fluidized bed 11. As a result, the decomposition of cyclohexanone oxime in the mixture is suppressed. The injection amount of the mixture into fluidized bed 11 is preferably in the range of from about 50 kg/h to about 1,000 kg/h per 1 m$^3$ of fluidized bed 11.

Figure 2:
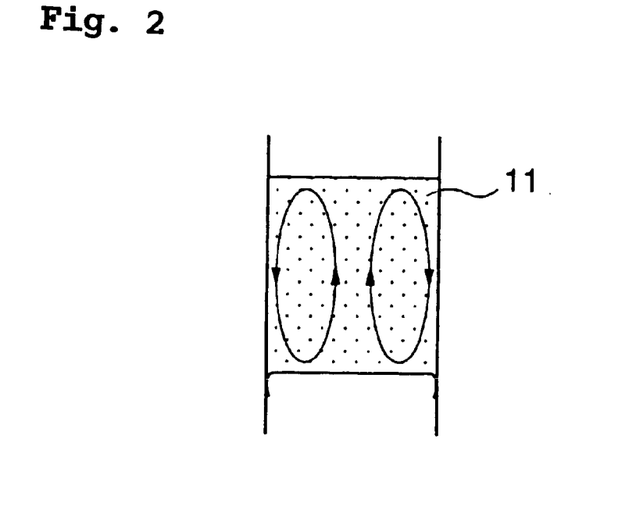
FIG. 2 illustrates a flow of inert particles in a fluidized bed with arrows showing the direction of the flow.

As described above, the cyclohexanone oxime and the solvent are evaporated in component 2 when injected into fluidized bed 11 of the inert particles which are sufficiently heated. The flow of the inert particles in fluidized bed 11 in component 2 is shown in FIG. 2 with arrows therein showing the direction of the flow. The inert particles are continuously replaced in the vicinity of injecting ports 7, 7 and are reheated by an external heat source and/or internal heat source which is/are installed in component 2. As a result, the mixture of cyclohexanone oxime and the solvent, which is continuously injected into the fluidized bed 11, is rapidly spread and evaporated on/over the surface of the heated inert particles, thereby suppressing the generation of side products of the mixture.

Examples of the external heat source include a heat jacket which is attached to the outer peripheral surface of component 2 and has a heat medium therein. Examples of the internal heat source include a heat exchanging pipe which is inserted into component 2.

When the flow of the inert particles is slow, the inert particles in the vicinity of injecting ports 7, 7 may be cooled down due to heat of evaporation. In order to suppress such cooling, the flow rate of the inert gas for fluidizing the inert particles is preferably adjusted at an appropriate rate. The flow rate of the inert gas into the column may be adjusted in the range of from a superficial fluid rate at minimum fluidizing conditions to a terminal rate of falling particles.

The mixture of cyclohexanone oxime directly injected into fluidized bed 11 is spread on the surface of the heated inert particles as a thin film of the mixture. The inert particles have heat energy in an amount necessary for evaporating the thin film of the mixture and, therefore, the heat energy is transferred to the film so as to evaporate the mixture. In such a way, in the present invention, a large amount of energy can be efficiently utilized in the evaporation of the mixture, since the thermal conductivity between liquid (i.e., the mixture) and solid (i.e., the inert particles) is higher than that between gas and liquid.

An inert gas (such as nitrogen gas) is forcibly supplied into fluidized layer 11 through gas introducing pipe 12 at the bottom of the column and flows upwardly in fluidized bed 11. As the inert gas flows in fluidized bed 11, the pressure of the gas (including the inert gas, the evaporated cyclohexanone oxime and the evaporated solvent) tends to drop. When, even in such a pressure drop, the pressure of the inert gas is enough to support the inert particles and to maintain fluidized bed 11 in the same region, fluidized bed 11 is in a so-called initially fluidized state. When the pressure is larger than that, fluidized bed 11 expands depending on the pressure. Fluidized bed 11 thus prepared has properties similar to those of liquid. For example, even when the column containing fluidized bed 11 is tilted, the upper surface of fluidized bed 11 remains horizontal. In addition, fluidized bed 11 hardly prevents objects from floating on the surface thereof.

A fluidized system such as fluidized bed 11 has a number of useful properties. Among them, easy temperature control and large heat conduction are very important in the present invention. An ideal fluidized system has no temperature gradient.

The inert particles in fluidized bed 11 are heated in an outer periphery of the column with an external heat source and/or internal heat source. The heated particles are circulated by the flow of the inert gas passing through fluidized bed 11 so as to be transferred to the center of the evaporator and then release the heat energy enough to evaporate the mixture of cyclohexanone oxime. Bubbles of the inert gas are formed only at the center of the column. As the bubbles of the inert gas move upward in fluidized bed 11, the inert particles are also transferred upward (see, FIG. 2). When the mixture of cyclohexanone oxime evaporates, an additional gas is generated by the phase change of liquid to gas of the mixture. The additional gas accelerates the total rate of gas in the column and may transform fluidized bed 11 from an expansion state to a bubbling state, or from a bubbling state to a slugging state.

It is preferred that, when the mixture of cyclohexanone oxime evaporates, the temperature of fluidized bed 11 is monitored by temperature sensor 13 so as to be controlled. The temperature of fluidized bed 11 is preferably in the range of about 120° C. to about 250° C., and more preferably in the range of about 120° C. to about 180° C. In order to minimize the scattering of temperature in the column, the mixture of cyclohexanone oxime and the inert gas are preferably preheated prior to the injection to fluidized bed 11. Preheating of the inert gas prevents that a temperature gradient is formed along the direction of the height of fluidized bed 11, which makes temperature control of fluidized bed 11 be easier.

The bubbling state or slugging state of fluidized bed 11 may be adjusted depending on the type of the columns which differ in structure or in height of fluidized bed therein. The adjustment may be conducted, for example, by changing the rate of injection of the inert gas or by adjusting a particle diameter and/or a bulk density of the inert particles.

Figure 3:
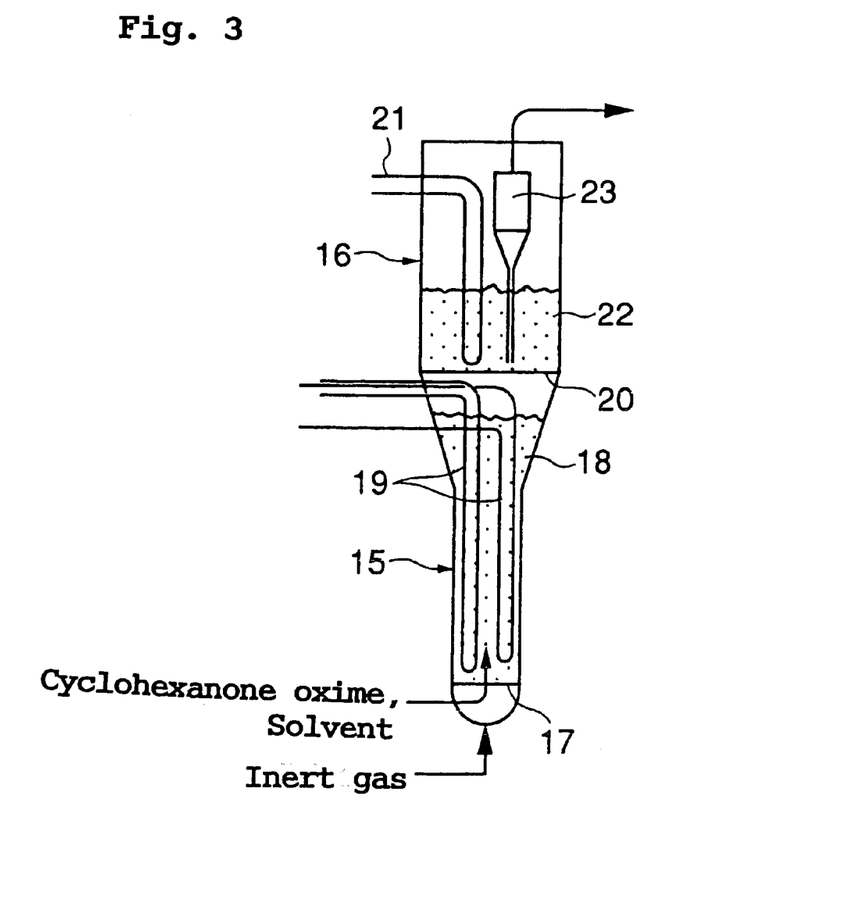
FIGS. 3 and 4 illustrate sectional views of examples of apparatus for conducting the present invention.
Figure 4:
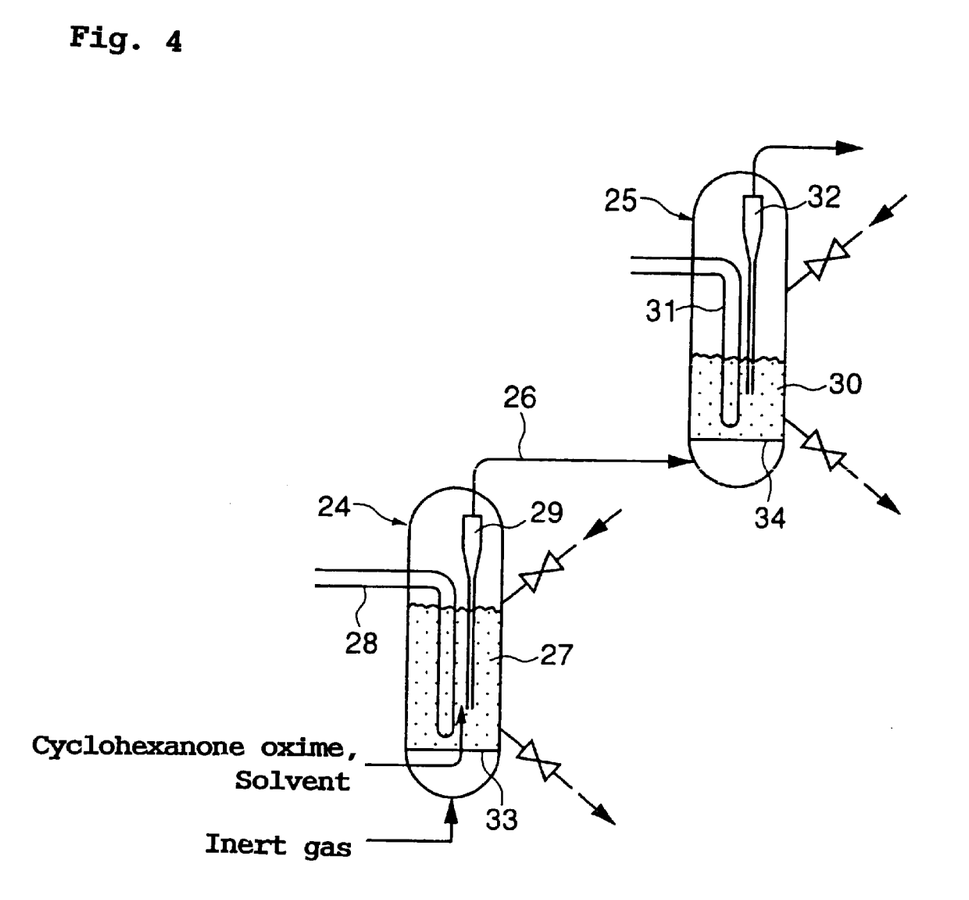
Figure 5:
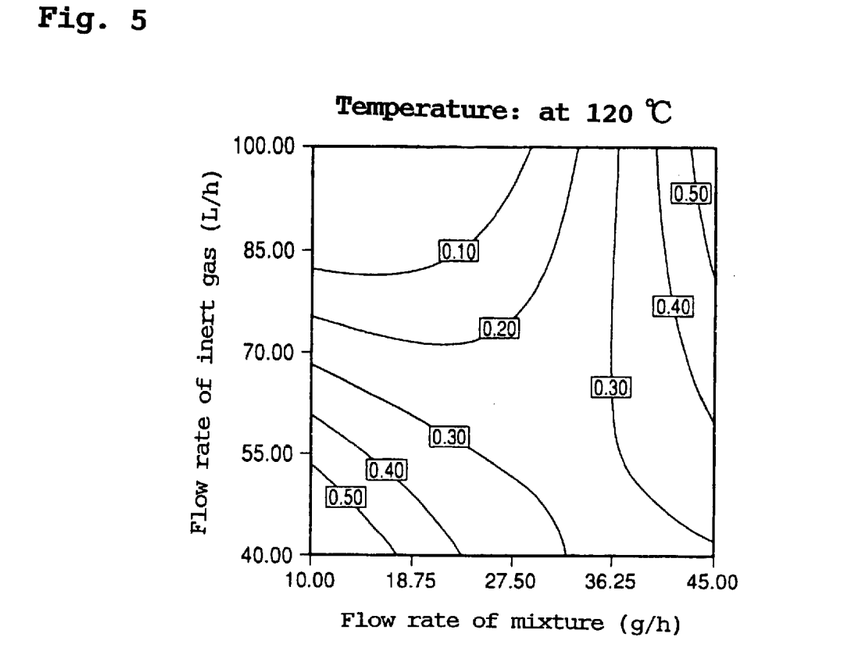
FIGS. 5, 6, 7 and 8 are graphs plotting conversion to side products which were generated in evaporation of cyclohexanone oxime at 120° C., 140° C., 160° C. and 180° C., respectively. The evaporation in FIGS. 5–8 was conducted in the present invention under the conditions in Example 1.
Figure 6:
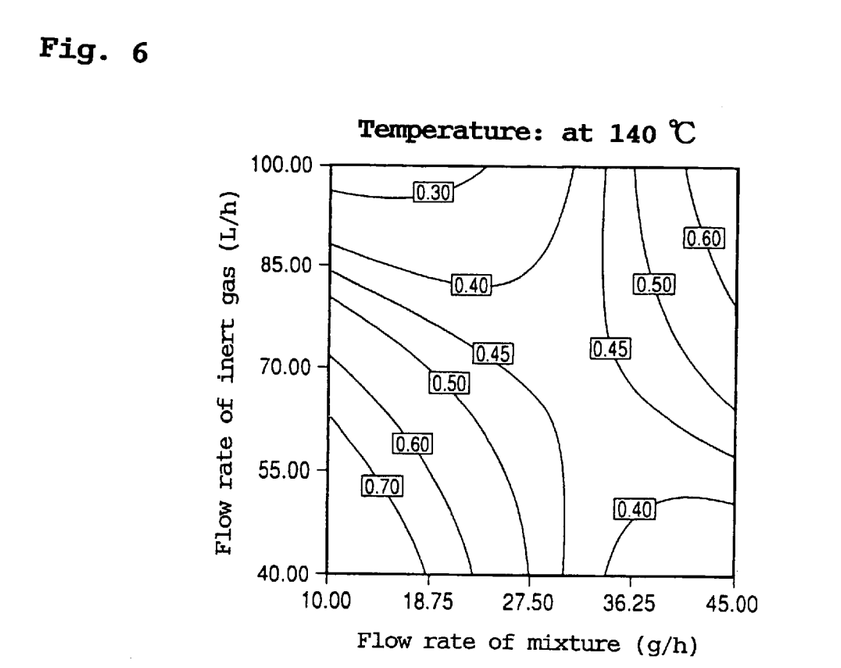
Figure 7:
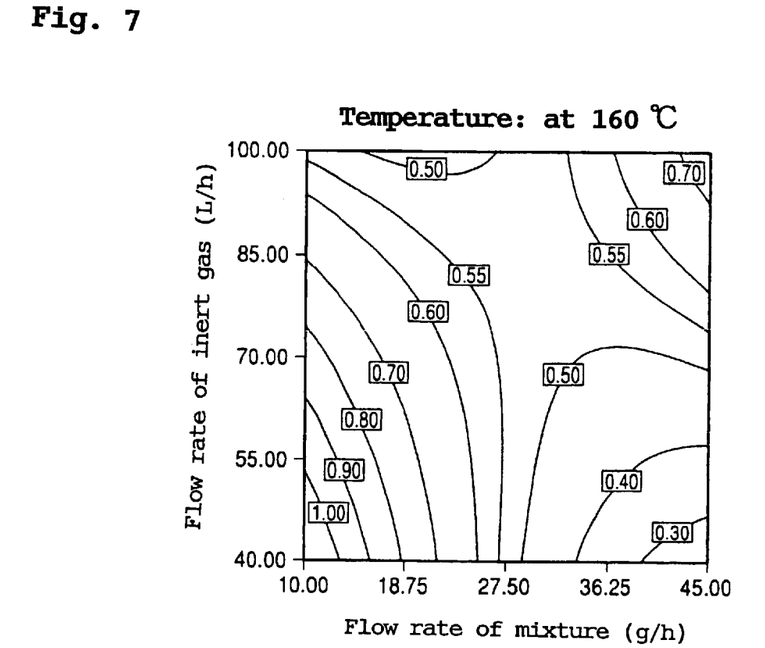
Figure 8:
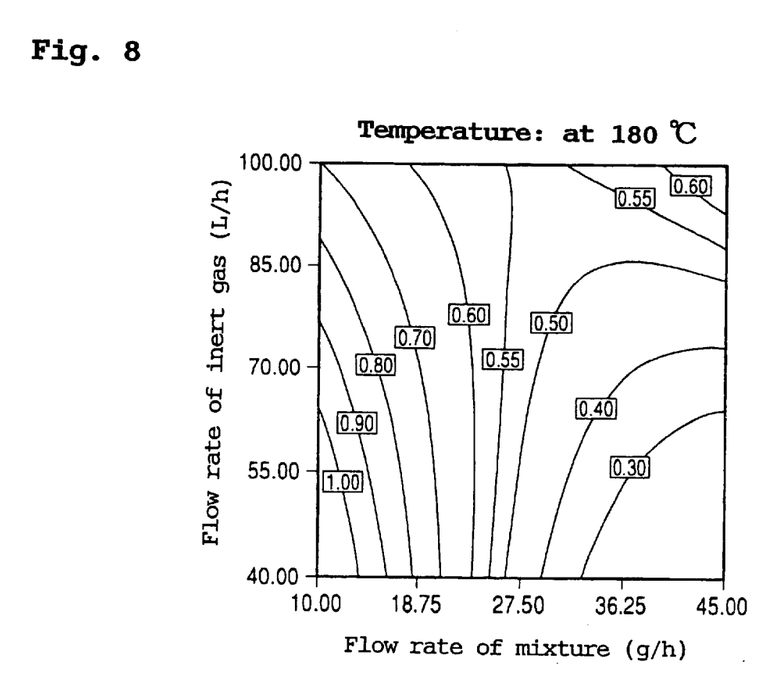
Figure 9:
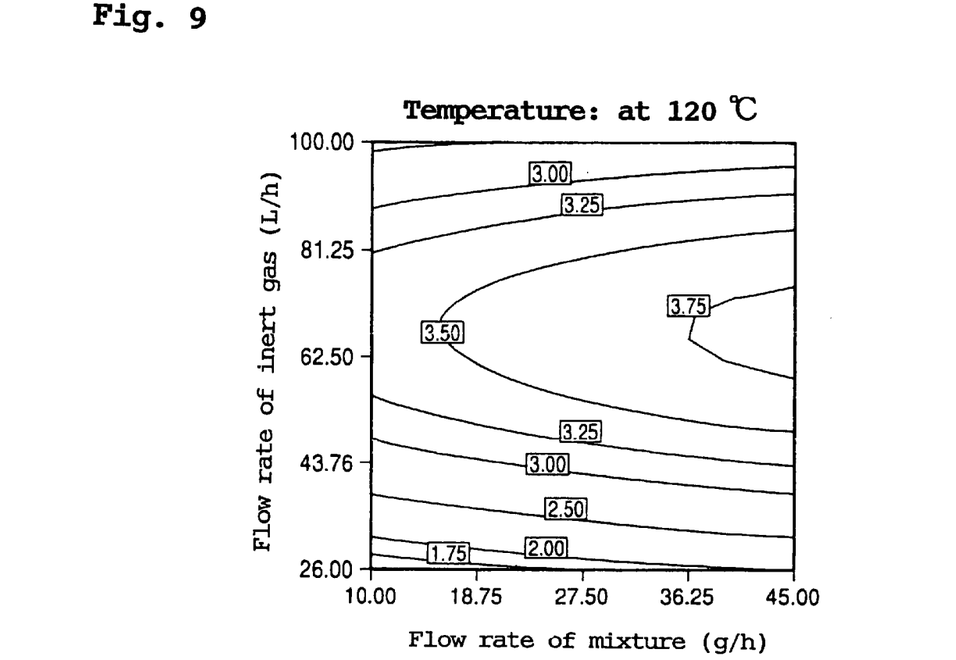
FIGS. 9, 10, 11 and 12 are graphs plotting conversion to side products which were generated in evaporation of cyclohexanone oxime at 120° C., 140° C., 160° C. and 180° C., respectively. The evaporation in FIGS. 9–12 was conducted under the conditions in Comparative Example 1.
Figure 10:
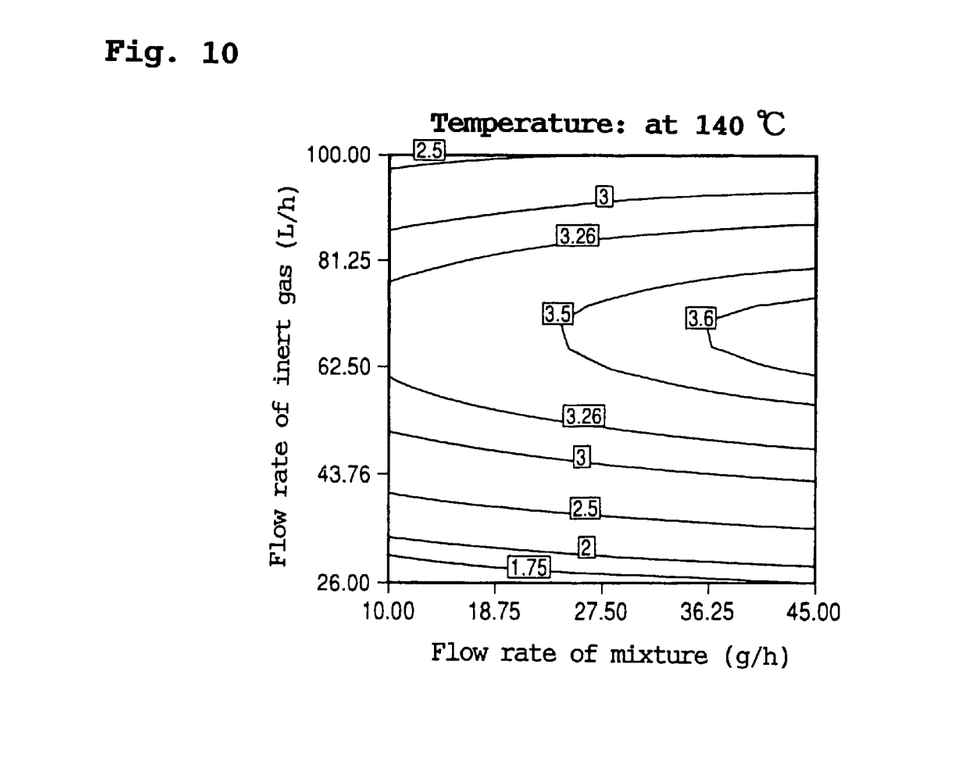
Figure 11:
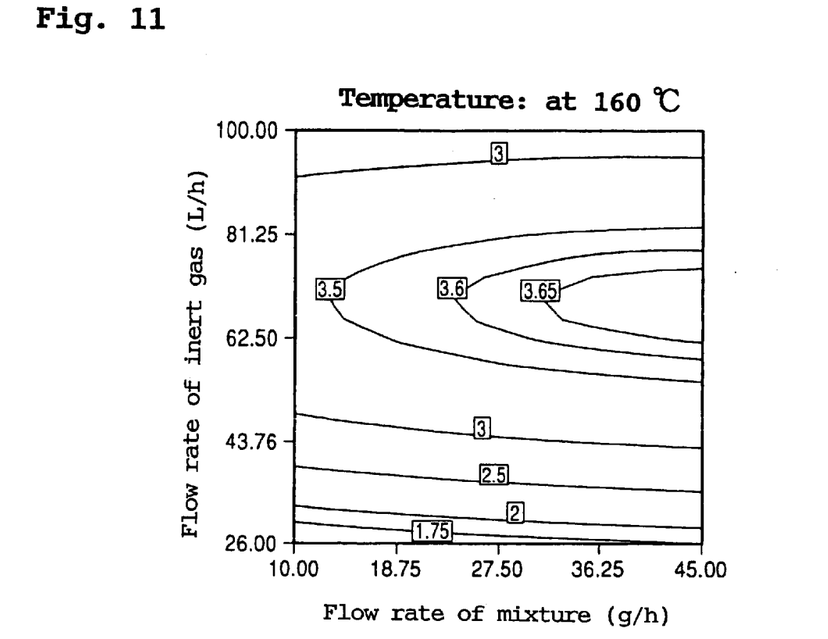
Figure 12:
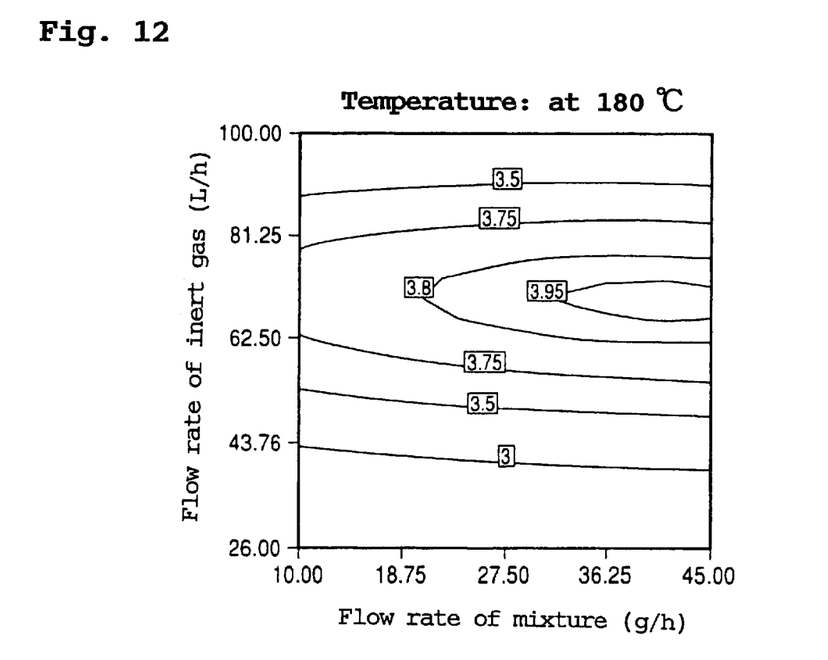

FIG. 3 and FIG. 4 (which also should not be construed as a limitation upon the scope of the present invention) illustrate sectional views of examples of the apparatus comprising an evaporation zone (or evaporator) and a reaction zone (or reactor) for conducting a production process in the present invention.

The apparatus shown in FIG. 3 has an evaporation zone and a reaction zone in a single column. In evaporation zone 15, the mixture of cyclohexanone oxime and a solvent is evaporated. In reaction zone 16, the evaporated cyclohexanone oxime in the mixture is rearranged into ε-caprolactam by gas phase Beckmann rearrangement reaction using a solid catalyst.

Evaporation zone 15 and reaction zone 16 are placed in a lower part and an upper part of the column, respectively, and are separated from each other with gas disperser 20. The evaporated mixture of cyclohexanone oxime in evaporation zone 15 is supplied through gas disperser 20 to reaction zone 16. When the separation between evaporation zone 15 and reaction zone 16 is insufficient, the mixture of cyclohexanone oxime in a liquid state enter reaction zone 16, which may lower the selectivity to ε-caprolactam.

In evaporation zone 15, inert particles are fluidized by an inert gas which is introduced from the bottom of evaporation zone 15 through gas disperser 17, so as to prepare fluidized bed 18. The inert particles (such as glass particles) preferably have a small specific surface area, a large bulk density and a large energy capacity, as described above. Prior to the injection into evaporation zone 15, the inert gas is preferably preheated nearly to the evaporation temperature of cyclohexanone oxime in the mixture.

Heat-exchanging pipes 19, 19 (which are internal heat sources) are inserted into evaporation zone 15. By introducing a high-temperature medium into heat-exchanging pipes 19, 19, heat necessary for the evaporation of the mixture of cyclohexanone oxime is supplied to the inert gas and to the inert particles. Examples of the high-temperature medium include steam and the like. Instead of heat-exchanging pipes 19, 19 or together with heat exchanging pipes 19, 19, an external heat source may be utilized. Examples of the external heat source include a heat jacket which contains the high-temperature medium therein and the like. The external heat source may be installed around the outer peripheral surface of evaporation zone 15.

The evaporated mixture of cyclohexanone oxime and the solvent is introduced together with the inert gas through gas disperser 20 from evaporation zone 15 to reaction zone 16. The mixture and the inert gas fluidize catalyst particles (which is a solid catalyst) in reaction zone 16 to prepare fluidized bed 22 of the catalyst particles. The mixture of cyclohexanone oxime and the solvent comes in contact with the catalyst, to conduct gas phase Beckmann rearrangement reaction (a fluidized-bed-type gas phase catalytic reaction) of cyclohexanone oxime and to provide a reaction product containing ε-caprolactam. The reaction product is discharged from reaction zone 16 through cyclone 23.

In the reaction, temperature may be controlled with a heat exchanger such as heat-exchanging pipe 21 (which may be disposed within reaction zone 16) and/or a heat jacket (which may be disposed at the outside of reaction zone 16). The heat exchanger may be utilized for removing heat, since the gas phase Beckmann rearrangement reaction is an exothermic reaction. It is preferred that the heat removed out of reaction zone 16 is transferred to and dissipated in evaporation zone 15 via a heat medium.

When an evaporation zone and a reaction zone are in a single column, the two zones may be placed so as to be substantially separated from each other in any manner. In FIG. 3, reaction zone 16 is placed upper than evaporation zone 15 in a single column. Such a placement is preferred in order to prevent droplets of the mixture of cyclohexanone oxime from being introduced into reaction zone 16 and from coming in contact with the catalyst particles therein. Alternatively, the evaporation zone and the reaction zone may be substantially separated from each other automatically by utilizing the difference in bulk density and/or particle size between the inert particles for the evaporation and the catalyst particles for the reaction. For example, when inert particles having a high bulk density and catalyst particles having a low bulk density are put and fluidized together in a single column, the inert particles and the catalyst particles are fluidized separately from each other. As a result, the inert particles gather to make a fluidized bed of the inert particles for the evaporation zone at a lower part of the column, and the catalyst particles gather to make a fluidized bed of the catalyst particles at an upper part of the column, respectively. Specifically, when the inert particles having a bulk density of from about 1 kg/L to about 3 kg/L and the catalyst particles having a bulk density of from about 0.5 kg/L to about 0.7 kg/L are put and fluidized together in a single column, then the inert particles and the catalyst particles are separated from each other, respectively, staying at a lower part and at a upper part of the column. Likewise, when the inert particles having a large particle diameter and the catalyst particles having a small particle diameter are put and fluidized together in a single column, the inert particles gather and prepare a fluidize bed of the inert particles at a lower part of the column, and the catalyst particles gather and prepare a fluidized bed of the catalyst particles at an upper part of the column, respectively.

When an evaporation zone and a reaction zone are in a single column and the fluidized bed of inert particles in an evaporation zone is in a bubbling state or in a slugging state, there is a possibility in that the flow of the particles within the fluidized bed is vigorous and thus the particles might move to a reaction zone along with the evaporated mixture of cyclohexanone oxime and might has some adverse effects on cyclohexanone oxime and/or ε-caprolactam, undesirably. The apparatus shown in FIG. 3 has reaction zone 16 having a diameter (column diameter) larger than that of evaporation zone 15, by which the linear rate of the evaporated mixture moving together with the inert particles is lowered towards reaction zone 16 and prevents the inert particles from entering reaction part 16.

Also, such a larger diameter of reaction zone 16 is preferred in the point that the larger diameter of the reaction zone may keep a good fluidizing state of the catalyst particles, thereby suppressing an undesired bubbling state or slugging state of the fluidized bed of the catalyst particles.

The inert particles in evaporation zone 15 and the catalyst particles in reaction zone 16 may be regenerated by being discharged continuously or intermittently from each zone and being treated with an inert gas and/or oxygen-containing gas at a high temperature of from about 300° C. to about 600° C. so as to remove the carbonaceous materials which has generated on the surface of these particles over time.

The apparatus shown in FIG. 4, which is another example of apparatus for conducting the production process in the present invention, comprises evaporator 24, reactor 25 and pipe 26 connecting evaporator 24 with reactor 25.

An inert gas is introduced into evaporator 24 from its bottom through gas disperser 33 to prepare fluidized bed 27 of inert particles. A mixture of cyclohexanone oxime and a solvent is introduced from a lower part of fluidized bed 27. It is preferred that the inert gas, the mixture of cyclohexanone oxime and solvent are previously preheated nearly to the evaporating temperature of the cyclohexanone oxime in the mixture. Fluidized bed 27 is preferably in a bubbling state or in a slugging state.

Heat exchanging pipe 28 for heating may be installed in evaporator 24. The mixture of cyclohexanone oxime and the solvent is evaporated in evaporator 24 and is introduced together with the inert gas through pipe 26 into reactor 25 from its bottom at which gas disperser 34 is provided.

In reactor 25, fluidized bed 30 of catalyst particles is prepared by introducing the mixture of cyclohexanone oxime and the solvent and the inert gas. Heat exchanging pipe 31 for removing heat may be installed in reactor 25. In fluidized bed 30, cyclohexanone oxime is rearranged by gas phase Beckmann rearrangement reaction to provide a reaction product containing ε-caprolactam. The reaction product is discharged through cyclone 32.

In FIG. 4, heat exchanging pipe 28 for heating and heat exchanging pipe 31 for removing heat are connected with each other to transfer the heat generated by the exothermic reaction in reactor 25 via a heat medium to evaporator 24 so that the heat can be utilized for the evaporation of the mixture of cyclohexanone oxime in evaporator 24.

In accordance with the present invention, the generation of undesirable side products is suppressed during the evaporation of cyclohexanone oxime. Such suppression provides advantages such that cyclohexanone oxime is consumed efficiently with little waste in the production of ε-caprolactam and that post-treatment steps (such as a purification step for separating by-products (and side products) from ε-caprolactam) can be carried out easily.

The invention being thus described, it will be apparent that the same may be varied in many ways. Such variations are to be regarded as within the spirit and scope of the invention, and all such modifications as would be apparent to one skilled in the art are intended to be within the scope of the following claims.

EXAMPLES

The present invention is described by the following Examples, which are not intended to limit the scope of the invention in any way.

Example 1

An evaporator as shown in FIG. 1 was prepared on a mini-plant scale. Component 2 at the middle part of the evaporator was made of a steel pipe having an outer-diameter of 20 mm, an inner-diameter of 16 mm and a length of 120 mm. Component 2 was broadened at the upper part thereof to have an outer-diameter of 30 mm and an inner-diameter of 26 mm. In component 2, was placed 50 g of glass particles having a mean particle diameter of 500–700 μm and a bulk density of 2.4–2.6 g/ml.

An inert gas (nitrogen gas) was preheated to the prescribed temperature which is specifically shown below and was introduced into the evaporator to prepare fluidized bed 11 of the glass particles. Two introducing pipes 6, 6 (capillaries) were inserted from the upper end of component 2 to a depth of 11 cm. A mixture in which cyclohexanone oxime and ethanol were mixed at 1:9 (in ratio by weight) was injected into fluidized bed 11 through introducing pipes 6, 6, and was evaporated. The conditions of the evaporation were as follows:

(1) Temperature of fluidized bed 11: at 120–180° C.

(2) Flow rate of the mixture: at 10–45 g/h (3) Flow rate of the inert gas: at 45–130 L/h By changing each of above parameters (1) to (3), was examined effects of i) the temperature of fluidized bed 11, ii) the flow rate of the mixture and iii) the flow rate of the inert gas, onto the conversion to side products (such as 5-cyanopent-1-en). The side products are generated due to adverse reactions during the evaporation of cyclohexanone oxime. The conversion is a ratio (by weight) of the generated side products to the supplied cyclohexanone oxime. By measuring the amount of the side products in the mixture before and after the evaporation with gas chromatography, the amount of the generated side products is obtained. The conversion is calculated using the equation below:

$$\text{Conversion}(\%) = \text{the amount of the generated side products}/\text{the amount of the supplied cyclohexanone oxime} \times 100(\%).$$

The results are shown in FIGS. 5 to 8. FIGS. 5, 6, 7 and 8 are graphs plotting the conversion to the side products which were generated in evaporation of cyclohexanone oxime at 120° C., 140° C., 160° C. and 180° C., respectively. The numerals shown in the graphs represent the conversion to side products and are plotted with regard to flow rate of the inert gas in ordinate and with regard to flow rate of the mixture in abscissa.

The average conversion obtained in Example 1 was 0.69%.

Example 2

Cyclohexanone oxime was evaporated in the same manner as in Example 1 except that methanol was used instead of ethanol. The average conversion obtained in Example 2 was 0.78%.

Comparative Example 1

A pipe having an outer-diameter of 20 mm, an inner diameter of 16 mm and a length of 200 mm was packed with gauze to prepare a pipe evaporator. An inert gas (nitrogen gas) was preheated to the prescribed temperature below and was introduced into the pipe evaporator. Then, a mixture of cyclohexanone oxime and ethanol (1:9 in ratio by weight) was injected into the pipe evaporator and was evaporated therein. This method corresponds to the method which may be conducted in an industrial apparatus. The conditions of the evaporation were as follows:

(1)' Temperature in the pipe: at 120–180° C.

(2)' Flow rate of the mixture: at 10–45 g/h (3)' Flow rate of the inert gas: at 20–130 L/h By changing each of above parameters (1)' to (3)', was examined effects of the temperature in the pipe, the flow rate of the mixture and the flow rate of the inert gas on the conversion to the side products. The results are shown in FIGS. 9 to 12. FIGS. 9, 10, 11 and 12 are graphs plotting the conversion to the side products which were generated in evaporation of cyclohexanone oxime at 120° C., 140° C., 160° C. and 180° C., respectively. The numerals shown in the graphs represent the conversion to the side products and are plotted with regard to the flow rate of the inert gas in ordinate and with regard to the flow rate of the mixture in abscissa.

The average conversion obtained in Comparative Example 1 was 2.75%.

Comparative Example 2

A commonly used flash evaporator for mini-plant was utilized to conduct the following experiments. The flash evaporator was filled with an inert gas (nitrogen gas) and was preheated to the prescribed temperature below. A mixture of cyclohexanone oxime and ethanol (1:9 in ratio by weight) was introduced into the the flash evaporator using a pump. The flash evaporator was then heated to have an inner pressure exceeding a vapor pressure of the mixture. When the mixture passed through a choke therein, the inner pressure dropped from the high pressure to atmosphere pressure to evaporate a part of the mixture, momentarily. The conditions of the evaporation were as follows:

(1)" Temperature in the evaporator: at 120–160° C.

Figure 13:
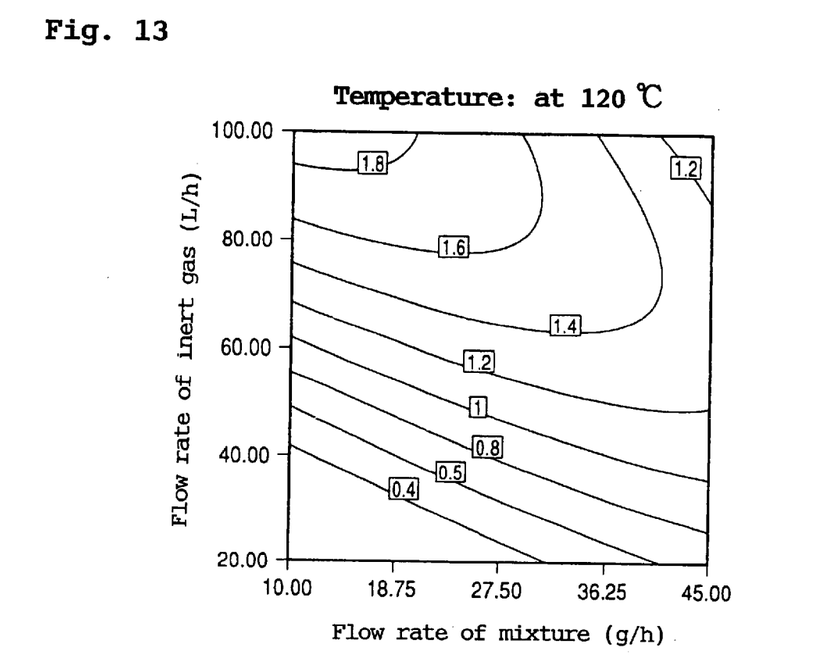
FIGS. 13, 14 and 15 are graphs plotting conversion to side products which were generated in evaporation of cyclohexanone oxime at 120° C., 140° C. and 160° C., respectively. The evaporation in FIGS. 13–15 was conducted under the conditions in Comparative Example 2.
Figure 14:
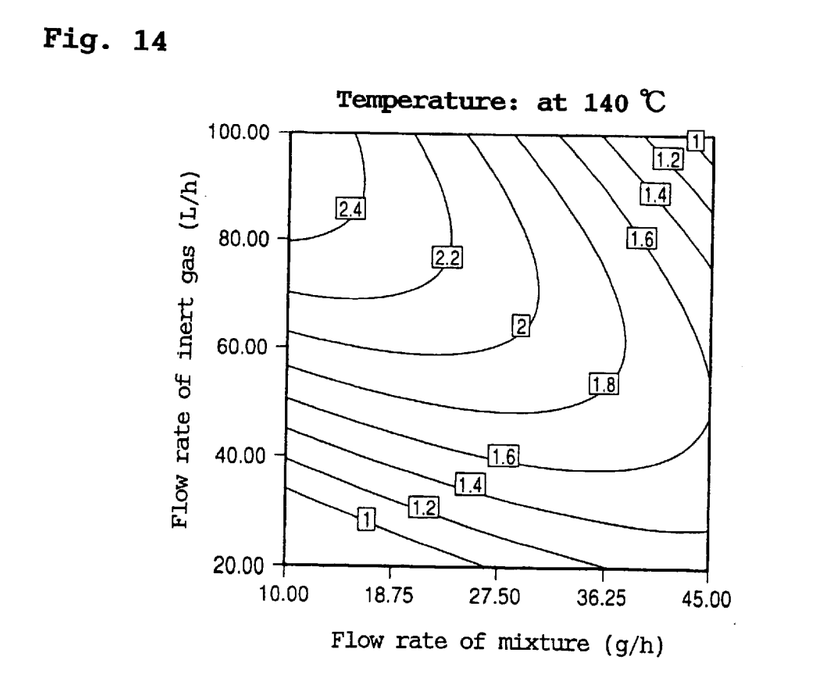
Figure 15:
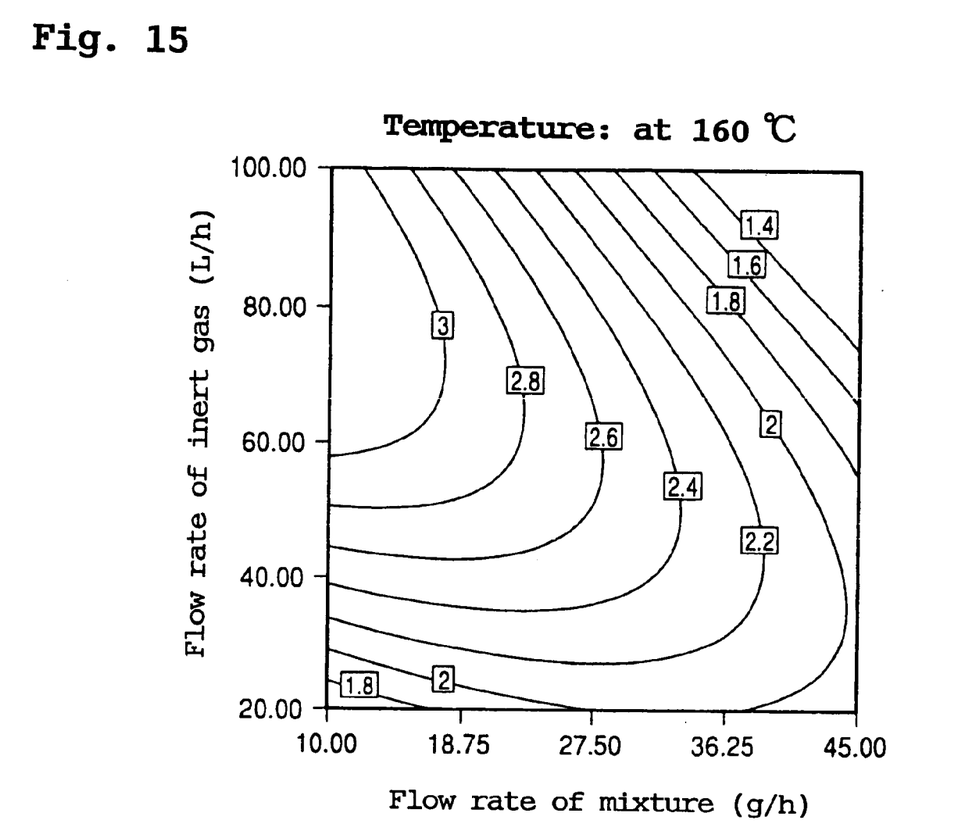

(2)" Flow rate of the mixture: at 10–45 g/h (3)" Flow rate of the inert gas: at 15–130 L/h By changing each of above parameters (1)" to (3)", was examined effects of the temperature in the evaporator, the flow rate of the mixture and the flow rate of the inert gas on the conversion to the side products. The results are shown in FIGS. 13 to 15. FIGS. 13, 14 and 15 are graphs plotting the conversion to the side products which were generated in evaporation of cyclohexanone oxime at 120° C., 140° C. and 160° C., respectively. The numerals shown in the graphs represent the conversion to the side products and are plotted with regard to the flow rate of the inert gas in ordinate and with regard to the flow rate of mixture in abscissa.

The average conversion obtained in Comparative Example 2 was 1.67%.

What is claimed is:

1. A process for producing ε-caprolactam comprising the steps of:

evaporating a mixture of cyclohexanone oxime and a solvent by injecting the mixture into a fluidized bed in which inert particles are fluidized by an inert gas, the particles having heat enough to evaporate the mixture;

rearranging cyclohexanone oxime in the evaporated mixture into ε-caprolactam by a gas phase Beckmann rearrangement reaction using a crystalline zeolite catalyst; and regenerating the inert particles by treating the inert particles with an inert gas and/or oxygen-containing gas at about 300° C. to about 600° C., wherein said solvent is a saturated alcohol having 1 to 6 carbon atoms.

2. the process according to claim 1, further comprising a step of regenerating the catalyst by treating the catalyst with an inert gas and/or oxygen-containing gas at about 300° C. to about 600° C.

3. The process according to claim 1, wherein the fluidized bed of the inert particles is in a bubbling state or in a slugging state.

4. The process according to claim 1, wherein the mixture and the inert gas are preheated prior to the introduction thereof to the fluidized bed.

5. The process according to claim 1, wherein the inert particles are continuously or intermittently circulated between the evaporation step and the regeneration step.

6. The process according to claim 1, wherein the rearrangement of cyclohexanone oxime is conducted in a fluidized bed in which the catalyst is fluidized by the evaporated mixture and the inert gas.

7. The process according to claim 2, wherein the rearrangement of cyclohexanone oxime is conducted in a fluidized bed in which the catalyst is fluidized by the evaporated mixture and the inert gas; and the catalyst is continuously or intermittently circulated between the arrangement step and the regeneration step.

* * * * *